United States Patent [19]

Mietzner et al.

[11] Patent Number: 4,681,761

[45] Date of Patent: Jul. 21, 1987

[54] **MAJOR IRON-REGULATED PROTEIN OF *NEISSERIA GONORRHOEAE* AND ITS USE AS VACCINE**

[75] Inventors: Timothy A. Mietzner; Stephen A. Morse, both of Atlanta, Ga.

[73] Assignee: State of Oregon, acting by and through the Oregon State Board of Higher Education, acting for and on behalf of the Oregon Health Sciences University, Portland, Oreg.

[21] Appl. No.: 790,910

[22] Filed: Oct. 24, 1985

[51] Int. Cl.$^4$ .............................................. C07K 15/04
[52] U.S. Cl. ..................................... 424/92; 530/350; 530/400; 530/416; 530/417; 530/825
[58] Field of Search ............. 260/112 R, 115; 424/92; 530/350, 400, 416, 417, 825

[56] References Cited

U.S. PATENT DOCUMENTS

| | | |
|---|---|---|
| 3,532,790 | 10/1970 | Greenberg et al. . |
| 3,577,527 | 5/1971 | Edwards . |
| 3,636,192 | 1/1972 | Gotschlich . |
| 3,855,197 | 12/1974 | Hirsch et al. . |
| 3,859,434 | 1/1975 | Jennings et al. . |
| 4,029,756 | 6/1977 | Gaafar . |
| 4,066,744 | 1/1978 | Price et al. . |
| 4,115,543 | 9/1978 | Wallace et al. . |
| 4,123,520 | 10/1978 | Hagopian et al. . |
| 4,134,214 | 1/1979 | Graham et al. . |
| 4,182,751 | 1/1980 | Ayme . |
| 4,203,971 | 5/1980 | Buchanan . |
| 4,220,638 | 9/1980 | Karkhanis et al. . |
| 4,229,530 | 10/1980 | Finkelstein et al. . |
| 4,235,994 | 11/1980 | Stoudt et al. . |
| 4,239,749 | 11/1980 | Buchanan et al. . |
| 4,241,045 | 12/1980 | Gaafar ...................... 260/112 R X |
| 4,271,147 | 6/1981 | Helting et al. . |
| 4,307,080 | 12/1981 | Kniskern et al. . |
| 4,351,761 | 9/1982 | Gaafar ........................... 260/112 R |
| 4,443,431 | 4/1984 | Buchanan et al. . |
| 4,451,446 | 5/1984 | Vandevelde et al. . |
| 4,459,286 | 7/1984 | Hilleman et al. . |
| 4,460,575 | 7/1984 | d'Hinterland et al. . |
| 4,461,838 | 7/1984 | Brinton et al. . |
| 4,497,900 | 2/1985 | Abram et al. . |

OTHER PUBLICATIONS

FEMS Microbiology Letters 4(1978), 71–75, Norqvist et al.
Infect. Immun. 36: 277–283 (1982), Blake et al.
Infect. Immun. 45: 410–416 (1984), Mietzner et al., (effective date Jul. 1984).
J. Exp. Med. 159:452–462 (1984), Blake et al.
Infect. Immun. 47:388–394 (Feb. 1985), West et al.

*Primary Examiner*—Howard E. Schain
*Attorney, Agent, or Firm*—Millen & White

[57] ABSTRACT

The major iron-regulated protein of a pathogenic species of the genus Neisseria, the gonococcal congener of which (MIRP) protein has a molecular weight of approximately 37,000 daltons and consisting of about 340 amino acids, is isolated in an immunospecific antigenically substantially pure form suitable for use as a vaccine against the pathogenic species of the genus Neisseria effective to stimulate the production of a protective level of antibodies to the pathogenic species in a susceptible host, by the steps of:

growing cells of that pathogenic species in an iron-depleted bacteriologic media;

harvesting the thus-grown cells;

disrupting the cells;

separating the soluble portion of the cells from the insoluble portion; and selectivity solubilizing the MIRP from the insoluble portion of the disrupted cells with an aqueous cationic surfactant aqueous media, e.g., cetyltrimethylammonium bromide; and removing residual contaminates in the MIRP fraction by chromatographic fractionation.

19 Claims, No Drawings

MAJOR IRON-REGULATED PROTEIN OF *NEISSERIA GONORRHOEAE* AND ITS USE AS VACCINE

This invention was made with Government support under contract #5 R01 AI3571-08 awarded by the National Institute of Allergy and Infectious Diseases. The Government has certain rights in this invention.

BACKGROUND OF THE INVENTION

This invention relates to the major iron regulated protein (MIRP) of *Neisseria gonorrhoeae,* in isolated immunospecific antigenically, substantially pure form, and its use as a vaccine.

The membrane proteins expressed by *N. gonorrhoeae* when grown under iron-limitation have been examined. Norquist et al, FEMS Microbiol. Letters 4:71-75 (1978), described the presence of several high-molecular-weight (70,000 to 100,000) membrane iron-regulated proteins. Subsequent studies have confirmed the presence of these high-molecular-weight iron-regulated proteins Mietzner et al, *Infect. Immun.* 45:410-416 (1984); West and Sparling, ibid, 47:388-94 (1985), as well as a previously unidentified iron-regulated protein with an apparent molecular weight of ca. 37,000. Although no attempt was made to isolate the protein in pure form, sodium dodecylsulfate-polyacrylamide gel electrophoresis visualized with a sensitive silver stain indicated that this protein represented a major component of Sarkosyl-insoluble membrane preparations from gonococci grown under iron-limited conditions. For this reason, this protein is referred to as the major iron-regulated protein (MIRP). Mietzner et al, supra. All gonococci examined to date express this protein under conditions of iron-limitation and peptide maps indicate that the structure of this protein is highly conserved among two unrelated gonococcal strains. West et al, ibid, 47:388-394 (1985), examined the expression of the gonococcal iron-regulated proteins and determined that they were not coordinately regulated. In the presence of various iron-containing proteins as iron-sources, different gonococcal strains expressed different combinations of iron-regulated proteins. The MIRP was expressed in the presence of all of the iron-containing molecules tested. Although the consistant expression of this protein under all conditions of iron-limitation and its conservation among gonococci prompted speculation that this protein might play a central role in iron-acquisition by the gonococcus, to date note direct function in iron-uptake has been ascribed to the MIRP.

Heretofore, no successful vaccine has been available having efficacy against the numerous strains of N.g. One of the principal problems which has impeded the production of a vaccine is the antigenic heterogeneity of the N.g. microorganisms.

A reported solution to this problem of antigenic heterogenicity is the use of the common peptide region from gonococcal pilin. Such a peptide region is not found in MIRP. Therefore, it was surprising to discover that the MIRP from the various species of the genus Neisseria nevertheless are antigenically homogeneous.

To facilitate an understanding of the MIRP of *N. gonorrhoeae,* a method was developed to purify this protein in reasonable quantities. This permitted the discovery of the ability of the purified MIRP to stimulate the production of monoclonal antibodies to gonococcal microorganisms and its utility as a vaccine to protect against gonococcal infections in susceptible hosts.

SUMMARY OF THE INVENTION

In a composition aspect, this invention relates to the MIRP of pathogenic species of the genus Neisseria, in isolated, immunospecific antigenically substantially pure form.

In another composition aspect, this invention relates to a vaccine against infection by a pathogenic species of the genus Neisseria, comprising, as its proteinaceous antigen component effective to stimulate the production of an immunizing level of antibodies to the pathogenic species in a susceptible host.

In another composition aspect, this invention relates to the isolated monoclonal antibodies to the MIRP protein.

In process aspect, this invention relates to a method for immunizing a susceptible host against infection by a pathogenic species of the genus Neisseria, which comprises administering to the susceptible host an amount of the MIRP, the isolated immunospecific antigenically substantially pure form effective to immunize that host.

In another process aspect, this invention relates to a method for isolation of the major iron regulated protein in substantially pure form.

DETAILED DISCUSSION

The isolation of the gonococcal MIRP in immunologically pure form was the result of the discovery that this protein can be separated from the proteins which are indistinguishable therefrom by ion exchange and/or gel chromatography by selective extraction of the MIRP from the gonococcal cells with a cationic surfactant at a fairly specific surfactant to total protein weight ratio. The optimum ratio for each specific surfactant can be determined by routine experimentation with whole cells or the soluble or crude membrane fraction thereof only, e.g., by the extraction of the whole cell or crude membrane fraction at various prior surfactant:protein ratios and determining by gel electrophoresis the minimum ratio which extracts substantially all of the MIRP. Usually, a surfactant:total protein weight ratio of about 0.25 to 0.75, preferably about 0.5, is required. The gonococcal MIRP is advantageously selectively solubilized with the cationic surfactant cetyltrimethylammonium bromide (CTB).

Conversely, the extraneous soluble materials can be selectively precipitated from the soluble portion of disrupted cells with the same surfactant under substantially the same conditions. The MIRP is retained in highly purified form in the supernatant. For maximum yield, the MIRP is separately selectively isolated from the crude membrane and from the soluble fraction of disrupted cells.

As is well known in the art, a cationic surfactant carries a positive charge on an amino or quaternary nitrogen thereof when dissolved in an aqueous medium. For increased water solubility, additional primary, secondary, or tertiary amino groups are generally present in the molecule or the amino nitrogen can be quaternized with low molecular weight alkyl groups such as methyl or hydroxyethyl.

The cationic surfactants fall generally into three broad clases, viz., (a) amines, both oxygen-free, e.g., acetate, naphthenate and oleate salts of aliphatic mono-, di-, and polyamines derived from fatty and rosin acids, including tertiary monoamines with $C_{18}$ alkyl or alkenyl chains and oxygen-containing amines, including amine oxides, ethoxylated alkylamines, 1-(2-hydroxyethyl)-2-imidazolines, and alkoxylates of ethylenediamine; (b) 2-alkyl-1-(2hydroxyethyl)-2-imidazoline surfactants, e.g., ethoxylated derivatives quaternized derivatives, e.g., with benzyl chloride, dimethyl sulfate, and other alkyl halides; and amine oxide derivatives; and (c) quaternary ammonium salts.

Of the foregoing classes of surfactants, the quaternary salts are preferred, especially the fatty alkyl, tri-loweralkylammonium halides.

According to amino acid analysis, the MIRP from *Neisseria gonorrhoeae* consists of 340 amino acids having approximately the profile set forth in Table I below. Of those amino acids 216 are neutral (19 of which are aromatic, 4 are sulfur containing and 17 are imino acids/protines) 76 are dicarboxylic acids and 48 are basic acids. Table II below sets forth the amino terminal 63 residues of the gonococcal MIRP. Included for comparison purposes in that table are the published N-terminal amino acid sequences of Protein I (PI) from strain R10 (Blake et al, 1984 supra) and Protein II (PII) molecules from strain R10 (a) and MS11 (b) (Blake et al, 1982, supra). The amino acid analysis detected a ratio of 2.2:1, aspartic acid to lysine, for the N-terminal residue. Therefore, aspartic acid is listed as this amino acid. All other residues were detected as pure compounds. The first five residues of the MIRP and Protein I show a great deal of homology. The amino acids which are in brackets indicate that their identity was determined by HPLC analysis but not confirmed by either GLC or TLC. The asterisk (*) indicates that the residue may be either cystine or cysteine.

MIRP congeners which are immunologically substantially identical to the gonococcal MIRP are expressed by the other pathogenic species of Neisseria, *N. meningitidis*, as well as by the non-pathogenic members *N. lactamica* and *N. cinerea*, when grown in an iron restricted environment and can be isolated in pure form by the same process as that employed to isolate the gonococcal MIRP. Although the amino acid profile and sequence of the various MIRP congeners may vary somewhat, these minor variations in the chemical structure of the various MIRP congeners does not affect their ability to stimulate the production of antibodies to the various pathogenic species of Neisseria in a susceptible host.

VACCINE

In its pharmaceutical composition of matter aspect, this invention relates to gonococcal vaccines, which due to the highly conserved antigenic structure of the MIRP, protect an otherwise susceptible mammalian host, which is preferably a human being, against gonococcal and related meningoccal infections. These vaccines can exist in the following forms:

1. A gonococcal vaccine based solely on the MIRP. Such vaccines may also contain an adjuvant, e.g., aluminum hydroxide gel, to enhance the immune response to the protein 2. A gonococcal vaccine containing other purified protein components, e.g., in addition to the MIRP, protein Is, and pili. Such a vaccine may also include an adjuvant, e.g., aluminum hydroxide gel.

3. A gonococcal vaccine in which the MIRP is a carrier to which is chemically bound a defined peptide, which thereby enhances the immunogenicity of the peptide, which peptide by itself would not be or would be only weakly immunogenic. The attachment of the peptide chemically to the MIRP enhances the latter's immunogenicity as well as stimulates production of anti-MIRP antibodies.

The vaccines of this invention are prepared from the antigenically substantially pure MIRP of this invention in storage stable, e.g., lyophilized, form. The formulation of a form suitable for clinical use can be conducted in a manner conventional for vaccines, e.g., sterile filtering of a solution thereof containing a bacteriostat, e.g., thimerosal, into conventional sterile vials, freeze-drying the sterile solution therein and capping the vial with conventional aluminum crimp seal cap with a removable lid covering a rubber stopper having hypodermically penetratable rubber membrane. Alternatively, a sterile solution containing about 25 ug of the MIRP per ml can be heat-sealed in glass vials, e.g., of 2 ml capacity having a fracturable neck. The lypholized product is regenerated with pyrogen-free sterile water to provide about 10 ug to 100 ug, preferably about 50 ug, per unit dose.

The vaccine according to the present invention may be administered by conventional techniques, including interperitoneal, intradermal, intravascular, and intravenous injection and local injection or topical application at the site of potential infection. Intramuscular and subcutaneous injections are believed to provide the most efficacious methods of admnistering the vaccine, particularly to humans. When the vaccine is administered by the above-identified preferred methods, the dosage is approximately 10 to 100 ug protein, with or without an adjuvant, such as aluminum hydroxide gel. The antibodies produced in the susceptible host prevent subsequent infection by pathogenic species of Neisseria, including gonorrhoeae.

To prepare a MIRP vaccine, lyophilized MIRP in immunospecific, antigenically substantially pure form is dissolved in phosphate buffered saline (PBS) at pH 7.0 to yield a solution containing 25 ug of MIRP per ml. The MIRP solution is sterilized by membrane filtration through an 0.22 u Millipore filter. The sterile vaccine is stored at 4° C. until needed.

The MIRP of this invention can be coupled with another antigenic polypeptide from the same or another pathogenic species of Neisseria in a conventional manner with a bifunctional coupling agent, e.g., dimethyl adipimidate diHCl or dimethyl pimelimidate diHCl, e.g., according to the procedure of New Hall et al., *Infection and Immunity* 28:785–791 (1980), whose disclosure is incorporated herein by reference.

As stated above, the major iron-regulated protein of *N. gonorrhoeae* has been previously reported in the prior art to be associated with crude membranes and Sarkosyl-insoluble membrane fractions. Silver-stained SDS-polyacrylamide gels of membrane proteins from gonococci grown under iron-limited conditions suggests that this protein existed in quantities comparable to that of Protein I. Analysis of the soluble fraction of cell sonicates indicates that the MIRP is present in ca. equal proportions to that in gonococcal membranes. The soluble MIRP is resistant to centrifugation at forces which normally pellet membranes. Under these conditions, nearly all of the Protein I (ca. 95%) is associated with the pellet. Proteins which are both membrane-bound and free have been observed in E. coli. These proteins are classified as binding proteins and are found within the organisms periplasmic space Lo, T.C.Y., *Can. J. Biochem.* 57:289–301 (1979). Analysis of the gonococcal periplasmic proteins using osmotic shock indicates that the gonococcal MIRP is not found in the osmotic shock fluid (unpublished data). Consequently, the possibility that this protein is localized in the periplasm is unclear. Another possibility is that the MIRP is loosely associated with the membrane and is released upon sonication. This could explain why no evidence was found for LPS being associated with the purified protein. Alternatively, the possibility that the MIRP is a soluble cellular protein which, due to its highly charged character, associates with membranes during the separation of the particulate and soluble fractions cannot be excluded. However, substantial quantities of this protein is observed in association with preparations of outer membrane blebs from gonococci grown in low-iron medium. Furthermore, the inability to remove the MIRP from membranes by extensive washing and its Sarkosyl-insoluble nature argue for its membrane association.

Surprisingly, it was discovered that the MIRP can be selectively solubilized from gonococcal membranes using the cationic detergent cetyltrimethyl ammonium bromide (CTB). Blake et al. (1982), supra, previously utilized this detergent at low-ionic strength to precipitate a fraction enriched for Protein I from whole gonococci. Nearly all the MIRP could be solubilized using these conditions. Under stringent conditions, a fraction enriched for the MIRP could be obtained at a CTB:protein ratio of 0.5 (w/w). Low concentrations of other types of detergents, such as Triton X-100 and Sarkosyl did not selectively solubilize the MIRP from membranes. At similar detergent to membrane protein ratios, CTB efficiently solubilizes gonococcal membrane phospholipids, which might be the mechanism by which MIRP is released from the gonococcal membranes.

Addition of CTB to the soluble whole cell sonicates under identical conditions as described above resulted in the formation of a precipitate. MIRP is the predominant protein species remaining in the cleared supernatants. CTB is known to preciptiate acidic polysaccharides under conditions of low-ionic strength. Presumably, it is this property which precipitates the nucleic acids, carbohydrates, and associated proteins which are found in the soluble fraction of sonicated whole cells. The highly soluble nature of the MIRP in CTB aqueous solutions results in the retention of this protein in the cleared supernatant.

The MIRP from crude preparations bound to CM-Sepharose and could be eluted using a gradient of NaCl. Binding of the MIRP to the cation exchange resin occurred, even in the presence of the cationic detergent CTB. The protein eluted as a single peak at ca. 150 mM NaCl. This fraction appeared to be substantially enriched by the criterion of a major band after analysis by SDS-PAGE. However, minor contaminating proteins with apparent molecular weights between 20,000 and 32,000 were associated with the MIRP-containing fraction. The presence of these proteins were variable from preparation to preparation. Blake et al (1984, supra) isolated Protein II using the same column matrix as was used from the purification of the MIRP. Protein IIs have been reported to have molecular weights of between 24,000 and 30,000. Swanson, J. *Infect. Immun.* 21:292–302 (1985). Therefore, contaminating Protein IIs can pose a problem in the purification of MIRP according to this invention. Therefore, to the extent possible, contamination with protein II molecules should be avoided by using transparent organisms for the original inoculum. However, the contaminating protein can usually be removed by molecular seive chromatography. Furthermore, gel filtration analysis indicates that the MIRP is eluted as a monomer. Protein I has previously been reported to exist as a trimer which interacts with detergent micelles. Blake et al., 1982, supra. Protein II also interacts with detergent micelles but elutes as a monomer (Blake et al. 1984, supra.) The gonococcal MIRP does not appear to interact with micelles in either of the detergents CTB or Zwittergent 3-14.

The highly charged nature of the MIRP was analyzed by isoelectric focusing. Difficulties in determining the isoelectric points for basic proteins are well-documented. In our system, the MIRP had a pI slightly greater than 9.35. However, the exact isoelectric point was not determined. Further evidence for the basic nature of the MIRP was its interaction with CM-sepharose at pH 8.0. In addition, the amino acid composition was similar to that of Protein II, which has a pI of between 9.0 to 10.0.

The first five amino acids of the MIRP are similar to the first five residues of Protein I. Hydropathic analysis of the 63 N-terminal amino acid residues of the MIRP indicates that it is a relatively hydrophillic segment. The major hydrophobic segment of the N-terminus appears to lie between the residues 15 and 30. Data from the amino acid composition indicates that this protein is lower in the proportion of aromatic amino acids than both Protein I and Protein II.

The MIRP of *N. gonorrhoeae* is reported in the prior art to be common to all strains examined. MIRP-specific rabbit antiserum and murine monoclonal antibodies were prepared and employed to analyze the antigenic conservation of the MIRP among members of the genus Neisseria. The results indicate that an antigenically related iron-regulated protein with a similar apparent molecular weight is present in all strains to *N. meningitidis*, *N. lactamica*, and *N. cinerea*. However, the remaining, nonpathogenic species of the genus Neisseria do not express a similar protein. The conservation of the MIRP, particularly among the pathogens *N. gonorrhoeae* and *N. meningitidis*, strongly suggests that this protein is associated with pathogenicity. Since the MIRP is apparently produced by gonococci in response to the lack of available iron in the environment, it is plausible to predict that this protein is a functional component of the gonococcal iron-uptake system. Simonson et al, *Infect. Immun.* 36:107–113 (1982), in examining iron uptake by *N. meningitidis*, determined that when membranes from iron-starved meningococci were incubated with $^{59}$Fe-citrate a large proportion of the iron remained associated with a protein complex which had an apparent molecular weight of 36,500. Whether or not the iron-regulated protein of meningococci, which is antigenically-related to the gonococcal MIRP, is involved in this association has not been analyzed. Conversely, experiments similar to those performed by Simonson have not been attempted for the gonococcus. However, both gonococci and meningococci may possess similar iron-uptake systems in which a conserved protein such as the MIRP may play a role. The availability of purified preparations of this invention of the MIRP will facilitate further investigation of this possibility.

Isolation of the gonococcal MIRP in substantially pure form permitted the determination that this protein stimulates the production of antibodies to pathogenic species of Neisseria in a susceptible host because of the use of the pure MIRP in immunological assays which measured MIRP-specific immunoglobins in infected humans. Non-infected humans lacked MIRP-specific immunoglobulins, thereby confirming the imunogenicity of MIRP.

The discovery that MIRP stimulates such antibody production permitted the discovery that susceptible hosts can be immunized against infection by not only the particular pathogenic species from which the MIRP was isolated but other pathogenic species of Neisseria as well.

Without further elaboration, it is believed that one skilled in the art can, using the preceding description, utilize the present invention to its fullest extent. The following preferred specific embodiments are. therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

PREPARATIONS

Media and reagents. GC agar medium (Difco Laboratories, Detroit, Mich.) supplemented with 1% (v/v) Iso Vitale-X (BBL Microbiology Systems, Cockeysville, Md.) and 0.5% (w/v) glucose was used for the routine maintainance of gonococci. Cultures were grown at 37° C. in a humidified atmosphere containing 4% $CO_2$. A previously described basal liquid medium was used for the growth of the organisms. Mietzner et al., (1984), supra. Analysis by atomic absorption spectroscopy indicated that this medium contained ca. 8.0 uM iron. In order to reduce the amount of free iron in the medium, 25 uM Desferal mesylate (Ciba-Geigy Corp., Summit, N.J.) was added. Gonococci are not able to remove iron bound to this chelator and thus, theoretically, the free iron in this growth medium is limited due to the excess Desferal. This medium is referred to as low-iron medium.

Sodium dodecyl sulfate (SDS), acrylamide, 2-mercaptoethanol, urea, molecular weight standards for SDS-polyacrylamide gels, and bromophenyl blue were obtained from BioRad Laboratories, Richmond, Calif.; Tris(hydroxymethyl)-aminomethane base (Tris buffer), cetyl-trimethylammonium bromide (CTB), Triton X-100, phenylmethylsulfonyl fluoride (PMSF), and ethylenediaminetetraacetic acid (EDTA) from Sigma Chemical Co., St. Louis, Mo.; N-2-hydroxyethyl piperazine-N'-2-ethane sulfonic acid (HEPES buffer) from Research Organics Inc., Cleveland, Ohio; Coomassie brilliant blue R-250 (Coomassie blue) from Bethesda Research Laboratories, Bethesda, Md.; Zwittergent 3-14 from Calbiochem, La Jolla, Calif.; Carboxymethyl (CM)-Sepharose CL-6B, Sephacryl S-3000, gel filtration molecular weight standards, and pI standards from Pharmacia fine chemicals, Piscataway, N.J. All other chemicals were of reagent grade.

Bacteria and Growth Conditions. All purification procedures and subsequent experiments utilized N. gonorrhoeae strain F62 provided by R. P. Williams (Baylor College of Medicine, Houston, Tex.) as the source of the MIRP. Transparent (Op-), non-piliated (P-) variants of this strain were selected and inocula prepared following growth on GC agar medium for 20 h. Gonococci from these plates were harvested and suspended in low-iron medium. This suspension was used to inoculate 300 ml Nephelometer flasks (Bellco Glass Co., Vineland, N.J.) containing 50 ml of the same medium to a density of ca. 25 Klett units (as monitored using a Klett-Summerson colorimeter with a #54 filter). The turbidity was measured at intervals during incubation at 37° C. in a gyratory shaker. Upon reaching mid-logarithmic phase, these suspensions were diluted 1:10 in low-iron medium. Incubation was continued until the culture reached late-logarithmic phase (100 to 120 Klett units) at which time the cells were harvested by centrifugation (10,000×g for 10 min at 4° C.).

Sodium dodecylsulfate-polyacrylamide gel electrophoresis (SDS-PAGE). SDS-PAGE was performed using the gel and buffer formulations described by Laemmli, U.K., Nature 227:680-5 (1970). The resolvino gel consisted of 10% acrylamide (w/v) and contained 70 mM NaCl as described by Mietzner et al., (1984), supra. All protein determinations were performed using the method of Markwell et al, Anal. Biochem. 87:206-210 (1978). Protein concentrations were adjusted to 1 mg/ml in a final sample buffer consisting of 62.5 mM Tris buffer, pH 6.8, 2% (w/v) SDS, 10% (v/v) glycerol, 0.001% (w/v) bromophenyl blue, and 5% (v/v) 2-mercaptoethanol. After dilution, samples were heated to 100° C. and held for 5 min. Electrophoresis was carried out using slab gels which were 140 mm long and 2 mm thick. A constant current (16 mA) was applied to the gel overnight at room temperature and electrophoresis was terminated when the dye front reached the bortom of the gel. The gels were stained for 2-12 hours in a solution of 0.1% (w/v) Coomassie blue in water:methanol:acetic acid (5:5:2). A 10% (v/v) acetic acid solution was used to destain the gels. Alternatively, gels were stained by the silver staining method of Tsai and Frasch, Analyt. Biochem, 119:115-6 (1982), modified by the omission of the periodate oxidation step. Development of the stain was terminated using a solution containing 10% (v/v) ethanol and 5% (v/v) acetic acid.

Cell fractionation. Bacteria harvested from 10 l of medium were washed once in Davis A defined medium (Difco). The cell pellet was suspended in 100 ml of 10 mM HEPES buffer, pH 7.4, containing 0.1% (v/v) protease inhibitor (10 mM PMSF in isopropanol). Aliquots of 5 ml were subjected to sonication for a total of 1 min using a high intensity sonifier (Branson Instruments Inc., Stamford, Conn.). This suspension was centrifuged at 48,000×g for 60 min. The pellet was enriched for cellular membranes while the supernatant contained primarily soluble proteins. Both the membrane and supernatant fractions were analyzed by SDS-PAGE for the proportion of the MIRP contained in each.

Selective solubilization of the MIRP from gonococcal membranes. The MIRP associated with the membrane fraction was selectively solubilized using the detergent CTB. Optimum ratios of detergent to membrane protein were determined as follows. Crude membranes were washed once in 10 mM HEPES buffer, pH 7.4, containing pretease inhibitor and pelleted by centrifugation (48,000×g for 60 min at 4° C.). The pellet was suspended in 10 mM Tris buffer, pH 8.0, to a final crude membrane protein concentration of 1 mg/ml. Increasing amounts of CTB, up to a final concentration of 0.8% (w/v), were added to 1 ml aliquots of the crude membrane suspensions. The detergent-membrane mixtures were incubated at room temperature for 20 min at which time the insoluble material was removed by centrifugation at 48,000×g for 60 min (room temperature). Equal volumes of the supernatants were analyzed by SDS-PAGE for the solubilized MIRP. The optimum detergent to protein ratio was defined as the lowest concentration of CTB which solubilized all of the membrane-associated MIRP.

Isolation of crude MIRP preparations. The pellet from sonicated whole cells was diluted to a final protein concentration of 1 mg/ml and CTB added to the optimum detergent:protein ratio. After incubation or 20 min at room temperature, the solubilized proteins were separated by centrifugation (48,000×g for 60 min at room temperature). The supernatant was enriched for the MIRP and was referred to as the crude preparation of the membrane-associated MIRP.

A similar method was used to obtain a preparation enriched for the MIRP associated with the supernatant fraction of sonicated whole cells. The supernatant fraction was diluted to a final protein concentration of 1 mg/ml in 10 mM Tris buffer, pH 8.0. To this suspension, CTB (0.05% final concentration) was added which resulted in the formation of a white precipitate. This mixture was incubated at room temperature for 20 min and the precipitate removed by centrifugation at 48,000×g for 60 min (room temperature). The resulting supernatant was enriched for the MIRP and was referred to as the crude preparation of the soluble MIRP.

Ion-exchange chromatography. Separation of proteins by ion-exchange chromatography was accomplished using the cation-exchange gel matrix CM-Sepharose 6B-CL. A 250 mm×20 mm column was prepared by washing the CM-Sepharose 6B-CL with two bed-volumes of 0.1 N NaOH followed by two bed-volumes of 1 M NaCl in 10 mM Tris buffer (pH 8.0) containing 0.05% (w/v) CTB. The column was then equilibrated with 5 bed-volumes of 10 mM Tris buffer containing 0.05% (w/v) CTB. The crude MIRP preparations were applied to the column and washed with the final equilibration buffer until all material not interacting with the column had eluted. A 0 to 1 M NaCl gradient in a total volume of 500 ml of the final equilibration buffer was used to elute proteins from the column. Fresh column packing was used for each purification. The column flow rate was maintained at 20 ml/h and the elution profile was followed by absorption at 280 nm using an in-line UV-2 monitor (Pharmacia). Fractions of 4 ml were collected.

Molecular seive chromatography. Sephacryl S-300 was used for gel filtration chromatography. A 850 mm×20 mm column was equilibrated and proteins were eluted with 10 mM Tris, pH 8.0, containing 0.05% (w/v) CTB and 0.3 M NaCl. Alternatively, gel filtration was used in a Zwittergent 3-14-containing buffer as described by Blake et al, (1982), supra. Samples for molecular seive chromatography were dialyzed overnight in the respective elution buffer. The dialyzed protein in a 2 ml volume was applied to the column and the flow rate was maintained at 30 ml/h. Fractions of 2.0 ml were collected and the protein absorption at 280 nm was followed. The molecular weight standards used were ferritin (440,000 daltons), catalase (232,000 daltons), bovine serum albumin (67,000 daltons), ovalbumin (43,000 daltons), chymotrypsinogen A (25,000 daltons), and ribonuclease A (13,700 daltons). Protein I from *N. gonorrhoeae* was purified as previously described by Blake et al, (1982), supra.

Analysis of fatty acids associated with the purified MIRP. Purified MIRP was analyzed for the presence of covalently bound fatty acids or tightly associated lipopolysaccharide (LPS) by gas liquid chromatography (GLC). The method used was a modification of a procedure described by Jarroll et al Molec. Biochem. Parisitol. 2:187-96 (1981). The purified MIRP preparation was diluted to 1 mg total protein per ml, dialyzed against 0.05% CTB in 10 mM Tris buffer, pH 8.0, and lyophylized. A preparation (250 ug protein) was rehydrated in 200 ul of distilled water and the protein precipitated by the addition of 1 ml ice-cold acetone. After incubation at −20° C. for 15 min, the suspension was subjected to centrifugation at 48,000×g for 20 min. The supernatant was removed and the precipitate was dried under a stream of nitrogen. Hydrolysis was accomplished by suspending the pellet in 4 N HCl and heating at 100° C. for 5 h. The hydrolysate was evaporated under a stream of nitrogen. The residue was esterified by adding 1 ml of $BF_3$/methanol and incubated at 80° C. for 5 min. After cooling, the suspension was extracted twice with 1.0 ml hexane:chloroform (4:1). After phase separation, the hexane:chloroform was removed, combined, and evaporated under nitrogen. Chloroform (10 ul) was used to resuspend the residue. This sample was analyzed by GLC using a Hewlett Packard 5840A reporting gas chromatograph with a flame ionization detector and a SP 2100 glass column (Supelco, Bellefonte, Pa.) as previously described by Jarroll et al, supra. To control for fatty acids contributed by the buffer, an identical preparation lacking the protein was analyzed.

Isoelectric focusing. Isoelectric focusing was performed using methods described by Laas et al, Analyt. Biochem. 101:449-461 (1980). Protein samples were dialyzed against 10 mM Tris buffer, pH 7.2, containing 6 M urea and 0.01% Triton X-100. Prepoured native polyacrylamide gels containing an ampholine mixture of 3.5 to 9.5 (LKB, Bromma, Sweden) were utilized. Determination of isoelectric points were made by using a mixture of standard proteins with known pI values.

Amino acid composition and N-terminal sequence analysis. Samples used for the amino acid composition and N-terminal sequence analysis were prepared from the membrane-associated fraction of the MIRP. The purified preparation from the gel filtration column was concentrated and dialyzed for 48 h at 4° C. against two changes of distilled water. This step resulted in the formation of a precipitate which was removed by centrifugation. The supernatant fraction retained 60% of the total protein in the original sample. The amino acid composition of the MIRP was determined by hydrolysis in 4N methanol-sulfonic acid, (Simpson et al, *J. Biol. Chem.* 251:1936–1940), in evacuated, sealed tubes at 115° C. for 22, 48, 72, and 96 h. The values for serine and threonine were corrected for destruction during hydrolysis by extrapolation to 0 time. The values for leucine, isoleucine, and valine were corrected for slow hydrolysis of the peptide bond by extrapolation to infinite time. Half-cystine and methionine were determined as cysteic acid and methionine sulfone, respectively, after performic oxidation.

Automated Edman degradation was performed with a Beckman 890C sequencer (Beckman Instruments, Palo Alto, Calif.), using a modified Quadrol program (No. 0011576) of Beckman Instruments in combination with polybrene. Thiazolinone derivatives of amino acids were converted to Pth-derivatives with aqueous 1.0 N HCl at 80° C. for 10 min. Pth-amino acids were identified by HPLC and confirmed by gas chromatography and/or thin-layer chromatography.

EXAMPLES

Example 1

Purification & Isolation of MIRP

Gonococci grown in low-iron medium were disrupted by sonication. After centrifugation, the pellet and supernatant fractions were analyzed for the presence of MIRP by SDS-PAGE.

A silver-stained SDS-PAGE analysis was made of the products of the purification steps used for the isolation of the gonococcal MIRP, i.e., the protein profile obtained from 5 ul of the whole cell sonicate, the protein profiles of the particulate and the soluble fractions, 5 ul each respectively, from sonicated whole cells (the pellet obtained from the centrifugation was suspended in a volume identical to that of the soluble fraction), protein profiles of the crude preparations from the membrane-associated and the soluble MIRP, respectively (these preparations were obtained after the soluble and particulate fractions from sonicated whole cells were diluted to 1 mg per ml in the extraction buffer (0.05% CTB in Tris, pH 8.0, 30 ul volumes of each extract were analyzed), and the pooled fractions of the crude membrane-associated MIRP and the crude soluble MIRP, respectively, after ion-exchange chromatography (a protein concentration of 15 ug was loaded in each well).

Under the conditions described, a significant proportion of the MIRP present in sonicated whole cells was found in the supernatant fraction and was resistant to centrifugation at 60,000×g for 90 min (data not shown). The MIRP which was associated with the particulate fraction was tightly bound because subsequent washings of the pellet did not remove detectable amounts of the protein.

The MIRP was completely solubilized by the addition of 2% (w/v) cetyltrimethylammonium bromide (CTB to the particulate fraction of sonicated whole cells. Other proteins in this crude membrane fraction were only partially solubilized at this CTB concentration. Therefore, the ability of lower concentrations of CTB to selectively solubilize the MIRP from the particulate fraction was examined, employing increasing concentrations of CTB (0% to 0.8%, w/v), on the solubilization of the MIRP. Nearly all of the MIRP was solubilized at a concentration of 0.05% (w/v) CTB. Therefore, a detergent:protein ratio of 0.5 (w/w) was used for preparing the crude membrane-associated MIRP.

An SDS-PAGE analysis was made of the selective solubilization of the gonococcal MIRP by CTB (stained with Coomassie blue). Crude membranes were incubated in the presence of CTB as described above at concentrations (% w/v) of 0, 0.0125, 0.025, 0.05, 0.1, 0.2, 0.4, and 0.8. Equal volumes (50 ul) were analyzed after separation of the insoluble material by centrifugation. At CTB concentrations of 0.0125% and 0.025%, the MIRP appeared to be selectively solubilized. Nearly all of the membrane-associated MIRP was solubilized at a CTB concentration of 0.05% (w/v). Under the conditions used, this concentration corresponded to a detergent:protein ratio of 0.5 (w/w). Subsequent purification steps utilized this ratio.

Using this same detergent:protein ratio, a similar crude preparation was obtained from the soluble fraction of the sonicated whole cells. Addition of the detergent resulted in the formation of a white precipitate which was removed by centrifugation. The resultant supernatant was enriched for MIRP.

The crude preparations were further purified by ion-exchange chromatography using CM-Sepharose 6B-CL. This sample could be applied in the buffer used to extract the MIRP (10 mM Tris buffer, pH 8.0, containing 0.05% CTB). At pH 8.0, the majority of the proteins did not bind to the column matrix and eluted in the void volume.

An elution profile of the CM-Sepharose column used to purify the MIRP from crude preparations was obtained by eluting the column, after the sample was applied, with a NaCl gradient of 0 to 1 M in a total buffer volume of 500 ml. Fractions (4 ml) were collected only through the first half of the gradient. Conductivity of the elution buffer was followed. The MIRP eluted as a single peak at a conductivity of 11 mMhos, which corresponded to a NaCl concentration of 150 mM. One major peak was resolved when a NaCl gradient of 0 to 1 M was applied to the column. A pink color was associated with the fractions comprising this major peak. When analyzed by SDS-PAGE and visualized by a sensitive silver stain, this peak was shown to contain the MIRP as a single predominant band along with a few minor contaminating proteins. The MIRP-containing peak was pooled, dialyzed against buffer (0.05% CTB in Tris, pH 8.0) and concentrated by lyophilization. Dialysis against this buffer did not remove or reduce the pink color associated with the sample. No difference in the elution profile were observed between the MIRP isolated from the soluble or particulate fractions of the whole cell sonicates (data not shown). In subsequent isolations, the crude extracts were pooled from both whole cell sonicate fractions for the ion-exchange chromatography step. A difuse peak associated with a component of the CTB resolved much later in the gradient (data not shown). Therefore, fractions were only collected through the first half of the NaCl gradient.

In order to remove the contaminating proteins, the pooled MIRP-containing fractions were subjected to gel filtration using Sephacryl S-300. This sample was lyophilized, suspended in a volume of 2 ml, and dialyzed against an elution buffer consisting of 10 mM Tris buffer (pH 8.0), 0.05% CTB, and 300 mM NaCl. The dialyzed preparation was applied to a Sephacryl S-300 column and chromatographed as described in the text. The following molecular weight standards were used for the calabration of the column: Ferritin, 440,000 daltons (440K); catalase, 238,000 daltons (232K); bovine serum albumin, 67,000 daltons (67K); ovalbumin, 43,000 daltons (43K); chymotrypsinogen A, 25,000 daltons (25K); and ribonuclease A, 13,700 daltons (13K). $V_o$ and $V_t$ were determined using blue dextran and vitamin $B_{12}$, respectively. The MIRP-containing peak had a Kav of 0.6 when the elution buffer consisted of 10 mM Tris (pH 8.0), 0.05% CTB, and 300 mM NaCl. This Kav corresponded to a molecular weight of between 26,000 and 32,000 daltons. After gel filtration the MIRP-containing fractions appeared to be pure by the criterion of a single band when analyzed by SDS-PAGE and visualized using a sensitive silver stain. A silver-stained SDS-polyacrylamide gel of a 10 μg sample of the purified MIRP-containing fraction after gel filtration was prepared and compared with a protein profile of whole gonococci, representing the starting material used for the isolation of the MIRP. No contaminating proteins were detected in the former preparation. Protein I has been reported to elute as a trimer in association with detergent micelles when an elution buffer consisting of 50 mM Tris (pH 8.0), 0.05% Zwittergent 3-14, 10 mM EDTA, and 200 mM NaCl was used. Blake et al (1982), supra. For comparison, the MIRP-containing fraction was dialyzed against this buffer and analyzed by gel filtration. The Kav of the MIRP-containing fraction under these conditions was identical to that obtained using the CTB-containing buffer (data not shown). Protein I eluted with a Kav which corresponded to a molecular weight of 188,000 under these conditions, similar to the value previously reported by Blake et al (1982), supra. The final yield of the MIRP using this procedure was dependent upon the degree of expression of this protein by *N. gonorrhoeae*. Typically, 10 to 20 mg of the MIRP could be isolated from 10 l of organisms grown in low-iron medium. This represented between 1 and 3% of the total cellular protein.

Isoelectric focusing. The purified MIRP preparation was analyzed by isoelectric focusing using an ampholyte gradient of 3.5 to 9.5.

In isoelectric focusing of the purified MIRP isolated from the soluble and the particulate fractions of sonicated whole cells, both purified preparations appeared to migrate at identical positions near the cathode. For this analysis, 20 ug of each purified protein preparation was focused. Under the conditions used, the MIRP appeared to migrate nearer the cathode than the pI standard trypsinogen (9.35).

Fatty acid analysis. Recently, evidence for the presence of proteolipids in *N. gonorrhoeae* has been reported. Chen et al, "The Pathogenic Neisseria", Am. Soc. Microbiol, Wash. D.C. (In Press). We analyzed the purified MIRP hydrolysate for the presence of fatty acids. Under the conditions employed, no detectable fatty acids were found. Furthermore, the absence of beta-hydroxy fatty acids in this analysis suggested that detecteble levels of LPS were not associated with the purified protein. The level of sensitivity in this assay theoretically could have detected one molecule of fatty acid per molecule of protein assuming 100% recovery of the fatty acids.

Amino acid composition. The predicted amino acid composition of the gonococcal MIRP is shown in Table I. Also included in Table I are the published amino acid compositions of two different Protein I molecules and a Protein II molecule. The amino acid composition of the MIRP is similar in character to the compositions of Proteins I and Protein II. However, the distribution of the individual amino acids is unique. Notably, the MIRP contains comparatively fewer aromatic amino acids and a greater number of proline residues than the proteins I and Protein II. Furthermore, the MIRP contains a higher proportion of basic amino acids than the Protein I molecules but a lower proportion than Protein II.

N-terminal amino acid sequence. The N-terminal amino acid sequence of the gonococcal MIRP is shown in Table II. This sequence is compared in Table II to the N-terminal amino acid sequences of other published gonococcal outer membrane proteins. Analysis of the N-terminal residue from the gonococcal MIRP detected aspartic acid and lysine in a molar ratio of 2.2:1, respectively. All subsequent residues were detected as single amino acids. The first five residues from the N-terminus of the MIRP and Protein I were nearly identical. Three of the five were identical and the two mismatched amino acids represented conservative changes in the DNA code. No other apparent homology between the gonococcal MIRP, Protein I, or Protein II was observed.

Example 2

Suspend 100 mg. purified MIRP in 50 mM triethanolamine, 5 mM MgCl$_2$ and 100 mM KCl, pH 8.5. Add an equimolar amount in the same buffer of the selected antigenic polypeptide, e.g., the peptide corresponding to residues 48 to 60 of the gonococcol pilin protein. See Schoolnick et al., J. Exp. Med. 159:1351 (1984) and Rothbard et al, J. Exp. Med. 160:208-221 (1984). Cross-linking is initiated by adding 20 mg/ml of dimethyl dipimidate in that same buffer. Incubate 30 min. at 23° C. and then quench by incubation for an additional 15 min. in the presence of 0.1 M ammonium chloride. Isolate the coupled product by gel chromatrography, e.g., that used for the purification of the MIRP.

Example 3

Dissolve 50 μg of lyophilized MIRP isolated from *N. gonorrhoeae* of this invention in 2 ml. of sterile pyrogen-free water, and inject IM into a susceptible adult human being. Repeat in one week. Measurement of antibodies to MIRP one month later will reveal an immunizing level thereof aqainst *N. gonorrhoeae* infection.

TABLE I

| Comparison of amino acid composition of purified gonococcal proteins | | | | |
|---|---|---|---|---|
| AMINO ACIDS | MIRP - | PI(MS11)[a] | PI(R10)[a] | PII(R10)[a] |
| Neutral | 216 (.64)[b] | 194 (.67) | 206 (.67) | 163 (.62) |
| Aliphatic | 176 (.52) | 156 (.52) | 162 (.53) | 147 (.56) |
| glycine | 27 | 33 | 42 | 32 |
| alanine | 54 | 27 | 27 | 26 |
| valine | 34 | 27 | 27 | 29 |
| leucine | 34 | 21 | 18 | 15 |
| isoleucine | 14 | 12 | 6 | 11 |
| serine | 4 | 21 | 27 | 21 |
| threonine | 9 | 15 | 15 | 13 |
| Aromatic | 19 (.03) | 24 (.08) | 27 (.09) | 10 (.04) |
| phenylalanine | 10 | 12 | 12 | 5 |
| tyrosine | 9 | 12 | 15 | 5 |
| Sulfur-containing | 4 (.01) | 5 (.02) | 5 (.02) | 5 (.02) |
| ½ cystine | 1 | 1 | 1 | — |
| methionine | 3 | 4 | 4 | 5 |
| Imino acids/proline | 17 (.05) | 9 (.03) | 12 (.04) | 1 (.003) |
| Dicarboxylic amino acids | 76 (.22) | 69 (.23) | 69 (.23) | 58 (.22) |
| aspartic/asparagine | 33 | 33 | 33 | 42 |
| glutamic/glutamine | 43 | 36 | 36 | 16 |
| Basic amino acids | 48 (.14) | 33 (.11) | 30 (.10) | 41 (.16) |

TABLE I-continued

| Comparison of amino acid composition of purified gonococcal proteins | | | | |
|---|---|---|---|---|
| AMINO ACIDS | MIRP - | PI(MS11)[a] | PI(R10)[a] | PII(R10)[a] |
| histidine | 6 | 6 | 6 | 4 |
| arginine | 15 | 9 | 6 | 22 |
| lysine | 27 | 18 | 18 | 15 |
| TOTAL | 340 | 296 | 305 | 262 |

[a]Data from Blake et al., J. Exp. Med. 159: 452-462 (1984); Inf. Immun. 36:277-283 (1982). (Designation in parenthesis indicates the strain from which the protein was isolated.)
[b]Values in parenthesis represent the proportion of residues which belong to the respective group of amino acids.

TABLE II

MIRP— 1                                               10
Asp Ile Thr Val Tyr Asn Gly Gln His Lys Glu Ala Ala Gln Ala Val Ala Asp →
     |   |   |   |
[PI  Asp Val Thr Leu Tyr Gly Ala Ile   Lys Ala Gly Val]

[PII[a]  Ala Gly Glu Asp Glu]

[PII[b]  Ala Ser Glu Glu Gly Arg Gly Pro Tyr]

MIRP— 20                                              30
Ala Phe Thr*Cys Ala Thr Lys Ile Lys Val Lys Leu Asn Ser Ala Lys Gly Asp →

MIRP— 40                                              50
Gln Leu Ala Gly Gln Ile Lys Glu Glu Gly Ser[Arg]Ser Pro Ala[Asp]Val Phe →

MIRP— 60
Tyr[Ser]Glu[His]Ile Pro[Arg]Leu Ala →

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In an isolated, immunospecific antigenically substantially pure form suitable for use as a vaccine, the major iron-regulated protein (MIRP) of a pathogenic species of the genus Neisseria, the gonococcal congener of which protein having a molecular weight of approximately 37,000 daltons and consisting of about 340 amino acids with the profile and initial amino sequence set forth in Tables I and II of the specification.

2. A protein according to claim 1 wherein the species is Neisseria gonorrhoeae.

3. A vaccine against the pathogenic species of the genus Neisseria effective to stimulate the production of a protective level of antibodies to the pathogenic species in a susceptible host, comprising, in admixture with a pharmaceutically acceptable carrier, as a proteinaceous antigen component thereof, the protein of claim 1.

4. The vaccine of claim 1, wherein the MIRP is from the species Neisseria gonorrhoeae.

5. The vaccine of claim 1, further comprising a pharmaceutically acceptable adjuvant effective to enhance the antibody production stimulated in the susceptible host by the protein.

6. The vaccine of claim 1, wherein the adjuvant is aluminium hydroxide gel.

7. The vaccine of claim 1, wherein the MIRP is chemically coupled to a polypeptide amino acid sequence comprises common antigenic regions of the gonoccocal pilin molecule or of gonoccocal protein I.

8. A method of immunizing a susceptible mammal against infection by a pathogenic species of the genus Neisseria, which comprises administering thereto an immunologically effective amount of a vaccine of claim 1.

9. A method according to claim 8, wherein the mammal is a human being.

10. A method according to claim 8, wherein the MIRP of the vaccine is from the species Neisseria gonorrhoeae.

11. A method according to claim 8, wherein the MIRP of the vaccine is from the species meningitidis.

12. A method according to claim 8, wherein the vaccine is administered intramuscularly.

13. A method according to claim 8, wherein the vaccine is administered subcutaneously.

14. A method according to claim 8, wherein the mammal is a human being, wherein the MIRP of the vaccine is from the species Neisseria gonorrhoeae, and wherein the vaccine is administered by injection.

15. In a method of producing the MIRP of a pathogenic species of the genus Neisseria which comprises the steps of:
 (a) growing cells of that pathogenic species in an iron-depleted bacteriologic media;
 (b) harvesting the thus-grown cells;
 (c) disrupting the cells;
 (d) separating the soluble portion of the cells from the insoluble portion;
the improvement which comprises
 (i) selectivity solubilizing the MIRP from the insoluble portion of the disrupted cells with a cationic surfactant aqueous media; and
 (ii) removing residual contaminates by chromatographic fractionation comprising cationic exchange chromatography in the presence of the cationic surfactant aqueous media; thereby isolating the MIRP in immunospecific antigenically substantially pure form.

16. The method of claim 15, wherein the surfactant is cetyltrimethylammonium bromide.

17. The method of claim 15, wherein the surfactant is employed at a surfactant:total protein weight ratio of about 0.25 to 0.75.

18. The method of claim 15, wherein the cationic exchange chromatography is followed by gel filtration.

19. The method of claim 15, wherein the MIRP is isolated from the soluble portion of the disrupted cells by selectively precipitating the extraneous material with a cationic surfactant from a buffer solution of the soluble portion at pH of about 8 and at surfactant:total protein weight ratio of about 0.25 to 0.75.

* * * * *